United States Patent [19]

Hadley et al.

[11] Patent Number: 5,189,047

[45] Date of Patent: Feb. 23, 1993

[54] 2-OXO-1,2-(DIHYDROPYRIDYL)-2H-1-BENZOPYRANS

[75] Inventors: Michael S. Hadley; Graham E. Jones, both of Harlow, England

[73] Assignee: Beecham Group p.l.c., England

[21] Appl. No.: 556,553

[22] Filed: Jul. 20, 1990

[30] Foreign Application Priority Data

Jul. 21, 1989 [GB] United Kingdom ............... 8916683

[51] Int. Cl.$^5$ .................. A61K 31/44; C07D 405/04
[52] U.S. Cl. .................. 514/337; 514/307; 514/299; 514/345; 514/277; 514/278; 546/269; 546/115; 546/116; 546/148; 546/183; 546/112; 546/301; 546/303; 546/290
[58] Field of Search ............... 546/269, 15.25; 514/337, 278, 277

[56] References Cited

U.S. PATENT DOCUMENTS 2,947,755  8/1960  Scudi et al. ................ 546/300
4,687,779  8/1987  Evans ..................... 514/456

FOREIGN PATENT DOCUMENTS 205292  12/1986  European Pat. Off. .
296975  12/1988  European Pat. Off. .

Primary Examiner—Jane T. Fan
Attorney, Agent, or Firm—Rosenman & Colin

[57] ABSTRACT

The present invention is directed to compounds of formula (I) and pharmaceutically acceptable salts thereof:

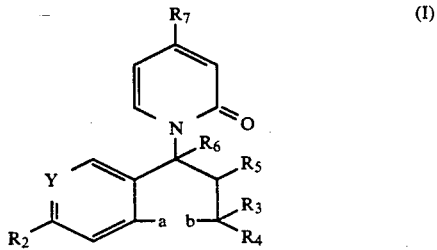

wherein Y, $R_2$, $R_3$, $R_4$, $R_5$, $R_6$, $R_7$, a and b are as defined in the Specification, having pharmacological activity, to a process for their preparation, and to their use as pharmaceuticals.

10 Claims, No Drawings

2-OXO-1,2-(DIHYDROPYRIDYL)-2H-1-BENZOPYRANS

This invention relates to novel compounds having pharmacological activity, to a process for their preparation and to their use as pharmaceuticals.

EP-A-296975 and 308792 (Merck Patent Gesellschaft) describe benzopyrans and pyranopyridines having pharmacological activity.

A novel group of compounds has been discovered, which compounds have a 2-oxo-4-phenyl-1,2-dihydropyridyl substituent at the 4-position (or equivalent position when the compound is other than a benzopyran or pyranopyridine). These compounds have been found to have blood pressure lowering activity, useful in the treatment of hypertension, and bronchodilator activity, useful in the treatment of respiratory tract disorders. In addition, these compounds are believed to be potassium channel activators which indicates that they are of potential use in the treatment of disorders associated with smooth muscle contraction of the gastro-intestinal tract, respiratory system, uterus or urinary tract including the ureter. Such disorders include irritable bowel syndrome and diverticular disease; reversible airways obstruction including asthma; premature labour; and incontinence, renal cholic and disorders associated with kidney stones. They are also indicated as of potential use in the treatment of cardiovascular disorders other than hypertension, such as congestive heart failure, angina, peripheral vascular disease, cerebral vascular disease, pulmonary hypertension and right heart failure. They may also be of potential use in the treatment of epilepsy.

Accordingly, the present invention provides a compound of formula (I) or a pharmaceutically acceptable salt thereof:

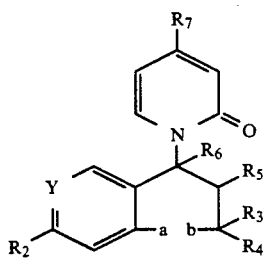

(I)

wherein a and b together form an —O— linkage or a bond or (when $R_2$ is hydrogen), $CH_2$;
either Y is N and $R_2$ is hydrogen; or
Y is $C-R_1$
wherein
either one of $R_1$ and $R_2$ is hydrogen and the other is nitro, cyano, halo, $CF_3$, $C_2F_5$, formyl, aldoxime, $CF_3O$, $NO_2$—CH=CH—, NC—CH=CH—; a group $R_xX$— wherein $R_x$ is $C_{1-6}$ alkyl, aryl or heteroaryl either of which may be optionally substituted by one, two or three of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, O.$SO_2$, CONH, O.CONH C=S, O.C=S, C=S.O, CH.SH, SONH, $SO_2NH$, O.SONH O.$SO_2NH$, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or a group $(R_wO)_2P(O)W$ wherein $R_w$ is hydrogen or $C_{1-6}$ alkyl and W is O or a bond; or $R_1$ is a $C_{3-8}$ cycloalkyl group or a $C_{1-6}$ alkyl group optionally substituted by a group which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino; and $R_2$ is hydrogen; or one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl; or $R_1$ and $R_2$ together with the carbon atoms to which they are attached, form 2,1,3-oxadiazole or triazole;
either one of $R_3$ and $R_4$ is hydrogen or $C_{1-4}$ alkyl and the other is $C_{1-4}$ alkyl; or
$R_3$ and $R_4$ together are $C_{2-5}$ polymethylene;
either $R_5$ is hydrogen, hydroxy, $C_{1-6}$ alkoxy or $C_{1-7}$ acyloxy or $ONO_2$; and
$R_6$ is hydrogen; or
$R_5$ and $R_6$ together are a bond;
$R_7$ is optionally substituted phenyl; and
the pyridonyl moiety is trans to the $R_5$ group when $R_5$ is hydroxy, $C_{1-6}$ alkoxy, $C_{1-7}$ acyloxy or $ONO_2$.

There is a group of compounds of formula (I) wherein a and b together form an —O— linkage; and either one of $R_1$ and $R_2$ is hydrogen and the other is nitro, cyano, halo, $CF_3$, formyl, aldoxime, $CF_3O$, $NO_2$—CH=CH—, NC—CH=CH—; a group $R_xX$— wherein $R_x$ is $C_{1-6}$ alkyl, aryl or heteroaryl either of which may be optionally substituted by one, two or three of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, O.$SO_2$, CONH, O.CONH, C=S, O.C=S, C=S.O, CH.SH, SONH, $SO_2NH$, O.SONH, O.$SO_2NH$, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or $R_1$ is a $C_{3-8}$ cycloalkyl group or a $C_{1-6}$ alkyl group optionally substituted by a group $R_9$ which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino and $R_2$ is hydrogen; or one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl.

In an alternative aspect of the invention, the aromatic ring containing Y may replaced by optionally substituted thiophene, as described in EP-A-360621 (Ortho Pharmaceutical).

When either one of $R_1$ and $R_2$ is hydrogen, the other is preferably selected from halo, $CF_3$, $C_{1-6}$ alkylcarbonyl, $C_{1-6}$ alkoxycarbonyl, nitro or cyano.

When one of $R_1$ and $R_2$ is nitro, cyano or $C_{1-3}$ alkylcarbonyl the other is, favourably, amino optionally substituted by one or two $C_{1-6}$ alkyl groups or by $C_{2-7}$ alkanoyl. In particular, when one of $R_1$ and $R_2$ is nitro, cyano or acetyl, the other is amino, methylamino, dimethylamino or acetylamino. Preferably, when one of $R_1$ and $R_2$ is nitro or cyano, especially cyano, the other is amino.

Halo substituents in $R_1$ and/or $R_2$ are usually chloro or bromo.

Values for $R_x$ when alkyl in $R_1/R_2$ are usually selected from methyl, ethyl, n- and iso-propyl, n-, iso-, secand tert-butyl, preferably methyl or ethyl. Suitable examples of other alkyl or alkyl containing groups in $R_1$ and in $R_3$ and $R_4$ when alkyl include those listed for $R_1$ and $R_2$ alkyl groups. When $R_1$ is alkyl, it is preferably selected from ethyl, iso-propyl and t-butyl.

A sub-group of $R_x$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrrolyl and pyridyl, in particular 2- and 3-furyl, 2- and 3-pyrrolyl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolinyl. Preferred examples of such groups include 2- and 3-benzofuranyl, 2- and 3-benzothienyl, and 2- and 3-indoyl, and 2- and 3-quinolyl.

Preferred examples of the groups or atoms for optional substitution of $R_x$ when aryl or heteroaryl include methyl, methoxy, hydroxy, chloro, nitro or cyano.

$R_1$ is preferably nitro, cyano, acetyl, $CF_3$, $C_2F_5$, methyl, ethyl, isopropyl, cyclopentyl or methylhydroxymethyl.

Preferably $R_3$ and $R_4$ are both methyl groups.

Suitable examples of $R_5$ when alkoxy include methoxy, ethoxy, n- and iso-propoxy, of which methoxy is preferred. When $R_5$ is $C_{1-7}$ acyloxy it is usually $C_{1-7}$ carboxylic acyloxy, such as $C_{1-7}$ alkanoyloxy wherein the alkyl moiety is usually as listed for alkyl in $R_1$ and $R_2$ above.

$R_5$ is favourably hydroxy or hydrogen, or $R_5$ and $R_6$ together are a bond.

Suitable values for substituents in $R_7$ phenyl include one, two or three substituents independently selected from $C_{1-6}$ alkyl, $C_{1-6}$ alkoxy, nitro, halo (such as fluoro, chloro, bromo), amino optionally substituted by one or two $C_{1-4}$ alkyl groups, $C_{1-6}$ alkylcarbonylamino, $C_{1-6}$ alkylcarbonyloxy, hydroxy and $C_{1-6}$ alkylcarbonyl. Suitable alkyl substituents or alkyl moieties is alkyl containing substituents are as listed hereinbefore for $R_x$.

Often $R_7$ is unsubstituted phenyl or phenyl substituted by a nitro or amino group.

Examples of pharmaceutically acceptable salts include acid addition salts with acids such as hydrochloric, hydrobromic, phosphoric, sulphuric, citric, tartaric, lactic or acetic acid.

The compounds of formula (I) wherein $R_6$ is hydrogen have at least one asymmetric centre and therefore exist in more than stereoisomeric form. The invention extends to each of these forms individually and to mixtures thereof, such as racemates.

The compounds of formula (I) and their salts may form solvates, such as hydrates, and there are included as part of the invention, wherever a compound of formula (I) or a salt thereof is herein referred to.

A preferred group of compounds within formula (I) is of formula (II):

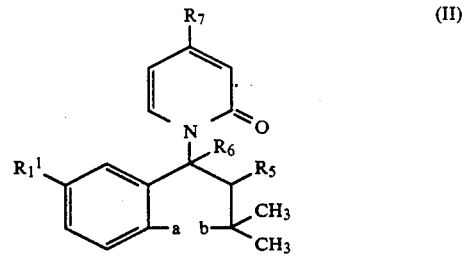

wherein $R_1^1$ is nitro, cyano, $CF_3$, $C_2F_5$, methyl, ethyl, isopropyl, cyclopentyl, methylhydroxymethyl or acetyl; and $R_5$, $R_6$ and $R_7$ are as defined in formula (I).

Suitable and preferred values for the variables are as described for the corresponding variables in formula (I).

The invention further provides a process for the preparation of a compound of formula (I) which comprises reacting a compound of formula (III):

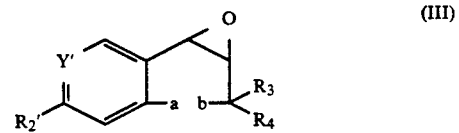

with an compound of formula (IV):

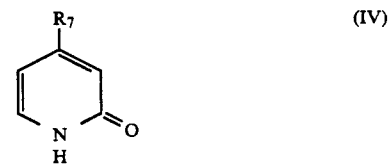

wherein $Y'$ and $R_2'$ are Y and $R_2$ respectively or moieties convertible thereto; and thereafter if desired or necessary converting $Y'$ and/or $R_2'$ to Y and/or $R_2$, converting $R_7$ to other $R_7$, converting the resulting $R_5$ hydroxy to other $R_5$ or to a compound wherein $R_5$ and $R_6$ together are a bond and/or optionally forming a pharmaceutically acceptable salt thereof.

The reaction is carried out under basic conditions, for example, using pyridine or a strong base, such as sodium hydride, although other bases such as potassium t-butoxide or tetrabutylammonium fluoride may also be used.

When strong bases are used, the reaction may be carried out in any suitable aprotic solvent, such as dimethylsulphoxide or tetrahydrofuran and when pyridine is used, it may take place in $C_{1-6}$ alkanols, such as ethanol. The reaction takes place at a temperature which provides a convenient rate of formation of the resulting compound of formula (I), usually from ambient to the reflux temperature of the solvent employed.

Conversions of $R_7$, $Y'$ to Y and $R_2'$ to $R_2$ are conventional in the art of aromatic chemistry.

The optional alkylation or acylation of the resulting compound of formula (I), wherein $R_5$ is hydroxy, to give another compound of formula (I), wherein $R_5$ is $C_{1-6}$ alkoxy or $C_{1-8}$ acyloxy, may be carried out in accordance with conventional alkylating or acylating reagents. For example, alkylation may be carried out using an alkyl iodide in an inert solvent, such as toluene, in the presence of a base, such as potassium hydroxide and acylation may be carried out using a carboxylic acid chloride or anhydride in a non-hydroxylic solvent in the presence of a base, for example, pyridine or triethylamine, or using the acid in the presence of a condensation promoting agent, such as dicyclohexylcarbodiimide.

$R_5$ hydroxy may be converted to $ONO_2$ according to the method described in WO 89/05808 (Beecham Group p.l.c.).

The optional dehydration of a resulting compound of formula (I), wherein $R_5$ and $R_6$ are hydroxy and hydrogen respectively, into another compound of formula (I), wherein $R_5$ and $R_6$ together are a bond, may be carried out by using a base, such as sodium hydride, in an inert solvent, such as dry tetrahydrofuran, at reflux temperature, or more preferably, using powdered sodium hydroxide in a solvent such as dioxan, at reflux temperature.

The reduction of an $R_5/R_6$ bond may be carried out by conventional catalytic hydrogenation using palladium on charcoal, although it is generally more preferable to prepare the compounds wherein $R_5$ and $R_6$ are both hydrogen by the method described in J. Med. Chem. 1990, Vol. 33, p492.

Pharmaceutically acceptable salts may be formed conventionally.

Compounds of formula (III) are known or prepared by analogous methods to those used for structurally similar known compounds.

They may be prepared as described in EP-A-76075, 91748, 207614, 205292, 214818, 250077 and 321175, all in the name of Beecham Group p.l.c., EP-A-314446 (American Home Products Corporation), WO 89/07103 and JO 2004/491/A (Nissan Chemical Industries Limited) and, if the aromatic ring containing Y is replaced by thiophene, as described in EP-A-360621 (Ortho Pharmaceutical).

As mentioned previously, the compounds of formula (I) have been found to have blood-pressure lowering activity and bronchodilation activity. They are therefore useful in the treatment of hypertension and/or respiratory tract disorders. They are also believed to be of potential use in the treatment of other disorders hereinbefore referred to.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive or bronchodilatory pharmaceutical composition which comprises an anti-hypertensive effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of spray, aerosol or other conventional method of inhalation, for treating respiratory tract disorders.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner. except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For transdermal administration, formulations suitable for topical use may be employed, optionally containing penetration enhancers.

The compositions may contain from 0.1% to 99% by weight, preferably from 10–60% by weight, of the active material, depending on the method of administration.

The compounds of formula (I) and pharmaceutically acceptable salts thereof are believed to show a synergistic effect with ACE inhibitor or β-blocker antihypertensive agents and such combination products, for concomitant or sequential administration, are within the present invention.

The present invention further provides a method of prophylaxis or treatment of hypertension or respiratory tract disorders in mammals including man, which comprises administering to the suffering mammal an antihypertensive or bronchodilatory effective amount of a compound of formula (I) or a pharmaceutically acceptable salt thereof.

An effective amount will depend on the relative efficacy of the compound, the severity of the disorder being treated and the weight of the sufferer. However, a unit dose form of a composition of the invention may contain from 0.05 to 500 mg of a compound of the invention and more usually from 0.1 to 50 mg, for example 0.5 to 25 mg such as 0.5, 1, 2, 5, 10, 15 or 20 mg. Such compositions may be administered from 1 to 6 times a day, more usually from 1 to 4 times a day, in a manner such that the daily dose is from 0.01 to 25 mg for a per kg body weight and more particularly from 0.1 to 10 mg/kg.

No toxicological effects are indicated at the aforementioned dosage ranges.

The present invention further provides a compound of formula (I) or a pharmaceutically acceptable salt thereof for use in the treatment or prophylaxis of hypertension and/or respiratory tract disorders.

The following descriptions relate to the preparation of intermediates and the following examples relate to the preparation of compounds of formula (I).

EXAMPLES

The following compounds were prepared.

| Compound | $R_5$ | $R_6$ | $R_a$ |
|---|---|---|---|
| E1 | a bond | | H |
| E2 | OH | H | 3-$NO_2$ |
| E3 | OH | H | 3-$NH_2$ |
| E4 | OH | H | 4-$NO_2$ |
| E5 | a bond | | 4-$NO_2$ |
| E6 | a bond | | 4-$NH_2$ |

Description 1

4-Phenyl-2-pyridone (D1)

A solution of 4-phenylpyridine-N-oxide (8.55 g, 50 mmol) in acetic anhydride (250 ml) was heated under reflux for sixteen hours. Acetic anhydride was then removed under vacuum and the residue was dissolved in absolute ethanol (200 ml) and 80% sodium hydride (1.5 g, 50 mmol) was added in small portions. The mixture was stirred for 2 hours under nitrogen, then evaporated and the residue was dissolved in ethyl acetate and dilute hydrochloric acid. The phases were separated and the aqueous phase was basified (sodium bicarbonate) and re-extracted (ethyl acetate). The aqueous phase was filtered to give the solid product which was recrystallised from ethyl acetate/methanol to give pure product, 3.76 g, Mp 226°-230° C. The combined organic extracts were evaporated to give a further quantity (1.58 g) of impure product.

Description 2 a) 4-(3-Nitrophenyl)pyridine-N-oxide (D2a)

Aqueous hydrogen peroxide (27.5 wt. %, 6.4 ml) was added to a solution of 4-(3-nitrophenyl)pyridine (5 g) in glacial acetic acid (50 ml), and the mixture was heated to approx 70° C. overnight. The mixture was then evaporated and the residue was triturated with ether. The product (6 g), still containing some acetic acid, was used without further purification. Mp 193°-196° C.

$^1$H NMR ($d_6$-DMSO) δ 7.80 (1H,t,J=8Hz), 7.94 (2H,d,J=6Hz) 8.27 (2H,m), 8.33 (2H,d,J=6Hz), 8.57 (1H,s)

b) 4-(3-Nitrophenyl)-2-oyridone (D2b)

A solution of compound D2a (6 g) and potassium acetate (2.94 g) in acetic anhydride (100 ml) was heated under reflux overnight. The mixture was then evaporated to dryness and the residue was dissolved in ethanol (100 ml). Sodium hydride (1.8 g) was added cautiously, and the mixture was stirred at room temperature for two days. Dilute hydrochloric acid was added to adjust the acidity to pH 3 before the mixture was evaporated to dryness. The residue was chromatographed on silica gel eluting with methanol/ethyl acetate (10%—50% MeOH). the eluted product was triturated with ether. Yield 0.4 g, Mp 250°-260° (decomp). 4-(3-Nitrophenyl)pyridine (1.7 g) was also recovered.

$^1$H NMR ($d_6$ DMSO) δ 6.60 (1H,dd,J=6 +1Hz), 6.72 (1H,d,J=1Hz), 7.52 (1H,d,J=6Hz) 7.78 (1H,t,J=8Hz), 8.17 (1H,d,J=Hz) 8.30 (1H,d,J=8Hz), 8.42 (1H,s)

Description 3

5 a) 4-(4-Nitrophenyl)pyridine-N-oxide (D3a)

Compound D3a was prepared according to the method of description 2a, starting from 4-(4-nitrophenyl)pyridine (12.3 g). Yield 6.1g, Mp. 210-212° C. (decomp).

$^1$H NMR ($d_6$ DMSO) δ 7.90 (2H,d,J=7Hz), 8.05 (2H,d,J=8.5Hz), 8.32 (4H,m).

b) 4-(4-Nitrophenyl)-2-pyridone (D3b)

Compound D3b was prepared according to the method of D2b, starting from compound D3a (6.1g) Yield 0.63 g, Mp. 268°-273° C.

$^1$H NMR ($d_6$ DMSO) δ 6.57 (1H,dd,J=6 +1Hz) 6.71 (1H,d,J=1Hz), 7.53 (1H,d,J=6Hz) 7.98 (2H,d,J=8.5Hz), 8.29 (2H,d,J=8.5Hz).

EXAMPLE 1

6-Cyano-2,2-dimethyl-4-(2-oxo-4-phenyl-1,2-dihydropyridyl)-2H-1-benzocyran (E1)

4-Phenyl-2-pyridone (0.43 g, 2.5 mmol) was dissolved in dry dimethylsulphoxide (10 ml) with warming. Sodium hydride (80% in mineral oil, 75mg) was added and the mixture was stirred for 1 hour at room temperature. 6-Cyano-2,2-dimethyl-2H-1-benzopyran-3,4-epoxide (0.5 g, 2.5 mmol) was added as dry solid and stirring was continued overnight. The mixture was then heated at 55°-60° C. for 4 hours, then cooled, diluted with water and extracted with ethyl acetate. The organic phase was dried and evaporated. The residue was chromatographed on silica gel eluted with ethyl acetate/petrol. Further chromatography in 5% methanol/chloroform was required to give the product, which was recrystallised from ether/pentane. Yield 0.15 g, Mp 159-160° C.

$^1$H NMR (CDCl$_3$) δ 1.63 (3H,s), 1.69 (3H,s), 5.90 (1H,s), 6.63 (1H,d,J=7Hz), 6.92 (1H,s), 6.98 (1H,d,J=7Hz), 7.10 (1H,s), 7.27 (1H,d,J=7Hz), 7.5-7.6 (4H,m), 7.7 (2H,m).

Mass spectrum (EI) m/z at 354 (M+) 339, 184, 171.

EXAMPLE 2

(±)-trans-6-Cyano-3,4-dihydro-2,2-dimethyl-4-(4-(3-nitrophenyl)-2-oxo-1,2-dihydropyridyl)-2H-1-benzocyran-3-ol (E2)

A solution of 6-cyano-2,2-dimethyl-2H-1-benzopyran-3,4-epoxide (0.36 g, 1.8mmol), 4-(3-nitrophenyl)-2-pyridone (0.6 g, 2.8mmol) and pyridine (0.12 ml) in dry ethanol (50 ml) was heated under reflux overnight. After cooling, the mixture was evaporated and the residue was partitioned between ethyl acetate and water. The organic phase was dried and evaporated and the residue was chromatographed on silica gel eluted with ethyl acetate to give the product (0.23 g, 31%), together with recovered epoxide (0.23 g) and pyridone (0.125 g). The product was further purified by trituration with ether. Mp 105°-107° C.

$^1$H NMR (CDCl$_3$) δ 1.40 (3H,s), 1.60 (3H,s), 3. d, J=10Hz), 6.39 (1H,d,J=10Hz), 6.58 (1H,dd,J=8 +2Hz), 6.90 (1H,d,J=2Hz), 7.00 (1H,d,J=8Hz), 7.10 (1H,d,J=8Hz) 7.15 (1H,s), 7.52 (1H,dd,J=8 +2Hz), 7.68 (1H,t,J=8Hz), 7.90 (1H,d,J=8Hz) 8.31 (1H,d,J=8Hz), 8.40(1H,s).

Mass spectrum (EI) m/z at 399 (M+-H$_2$O), 384 (M+-H$_2$O -CH$_3$) (CI) m/z at 418 (MH+)

EXAMPLE 3

(±)-trans-4-(4-(3-Aminoohenyl)-2-oxo-1,2-dihydropyridyl)-6-cyano-3,4-dihydro-2,2-dimethyl-2H-1-benzopyran-3-ol (E3)

Compound E2 (0.26 g, 0.6mmol) was stirred with tin (II) chloride (0.68 g, 3.6mmol) in ethanol (10 ml) at 75° C. for 1h. The mixture was cooled and poured onto ice, then basified with 5N ammonium hydroxide and extracted thoroughly with dichloromethane. The combined extracts were dried and evaporated to give the product (0.15 g, 64%), which was triturated with ether. Mp 153°-155° C. (decomp).

$^1$H NMR (CDCl$_3$) δ 1.39 (3H,s), 1.58(3H,s), 3.91 (1H,d,J=10Hz), 6.35 (1H,d,J=10Hz), 6.51 (1H,dd, J=8 +2Hz), 6.80(2H,broad s), 6.88 (1H,s), 6.93-7.00 (3H,m), 7.15 (1H,s), 7.23 (1H,t,J=8Hz), 7.51 (1H,dd,J=8 +2Hz).

Mass spectrum (EI) m/z at 387 (M+), 369 (M+-H$_2$O), 354 (M+-H$_2$O-CH$_3$)

EXAMPLE 4

(±)-trans-6-Cyano-3,4-dihydro-2,2-dimethyl-4-(4-(4-nitrophenyl)-2-oxo-1,2-dihydropyridyl)-2H-1-benzopyran-3-ol (E4)

Compound E4 was prepared by the method of example 2, starting from compound D3b (0.6 g, 2.8mmol). Yield 0.25 g, with 0.18 g D3b recovered. The product was recrystallised from ethyl acetate/petrol (60°-80° C.), Mp 278°-284° C.

$^1$H NMR (CDCl$_3$) δ 1.42 (3H,s), 1.62 (3H,s) 3.88 (1H,d,J=10Hz), 6.37 (1H,d,J=10Hz) 6.58 (1H,d,J=7Hz), 6.97 (1H,s) 7.00 (1H,d,J=8.5Hz), 7.11 (1H,d,J=7Hz), 7.52 (1H,d,J=8.5Hz), 7.79 (2H,d,J=7Hz) 8.38 (2H,d,J=8.5Hz)

Mass spectrum (EI) m/z at 399 (M+-H$_2$O), 384 (M+-H$_2$O-CH$_3$) (CI) m/z at 418 (MH+)

EXAMPLE 5

6-Cyano-2.2-dimethyl-4-(4-(4-nitroohenyl)-2-oxo-1.2-dihydropyridyl)-2H-1-benzopyran (E5)

Compound E4 (0.15 g, 0.36mmol) was stirred with powdered sodium hydroxide (0.10 g) in 1,4-dioxan (10 ml) at reflux temperature for 30 minutes. The mixture was filtered and evaporated and the residue was dissolved in ethyl acetate and washed with water. The organic phase was dried and evaporated, and the residue was subsequently recrystallised from ethyl acetate/petrol (60°-80° C.). Yield 0.096 g, Mp 217°-220° C.

$^1$H NMR (CDCl$_3$) δ 1.60 (3H,s), 1.65(3H,s), 5.88(1H,s), 6.55 (1H,dd,J=7 +2Hz), 6.92 (1H,d,J=2Hz) 6.95 (1H,d,J=8Hz), 7.04 (1H,d,J=2Hz), 7.30 (1H,d,J=7Hz), 7,49 (1H,dd,J=8 +2Hz) 7.80 (2H,d,J=8Hz), 8.39 (2H,d,J=8Hz)

EXAMPLE 6

4-(4-(4-Aminophenyl)-2-oxo-1,2-dihydrocyridyl)-6-cyano-2,2-dimethyl-2H-1-benzopyran (E6)

Compound E6 was prepared according to the method described for example 3, starting from compound E5 (70mg), Mp 215°-223° C.

$^1$H NMR (CDCl$_3$) δ 1.60 (3H,s), 1.65 (3H,s), 5.85 (1H,s), 6.55(1H,d,J=6Hz) 6.81 (1H,s), 6.85 (1H,d,J=6Hz) 6.90 (2H,d,J=8Hz), 7.05 (1H,s), 7.18 (1H,d,J=6Hz) 7.47 (1H,d,J=6Hz), 7.50 (2H,d,J=8Hz)

Mass spectrum (EI) m/z at 399 (M+-H$_2$O), 384 (M+-H$_2$O-CH$_3$) (CI) m/z at 418 (MH+)

PHARMACOLOGICAL DATA

Compounds of the invention were tested for activity in one or both of the following test methods.

1. Antihypertensive Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12-18 weeks) with systolic blood pressures >180 mmHg were considered hypertensive.

The compound of Example 1 gave a maximum fall in blood pressure of 27% at a dose of 0.3 mg/kg.

2. Bronchodilator Activity

Male guinea pigs (300–600 g) were stunned by a blow to the head and bled from the carotid artery. The trachea was exposed, dissected free of connective tissue, and transferred to oxygenated Krebs solution at 37° C. Next, spirals (2 per trachea) were prepared by cutting the whole trachea spirally along its longitudinal axis and then dividing this spiral lengthwise. Each preparation was mounted, using silk thread, in a 10 ml organ bath filled with Krebs solution at 37° C. and bubbled with 5% $CO_2$ with $O_2$. The resting tension of the preparations was set at 2 g and changes in muscle tension were monitored isometrically by means of a UFI (2 oz) force and displacement transducer (Ormed Ltd) connected to a Linseis pen recorder. All preparations were allowed to equilibrate for 60 minutes. During this equilibration period the preparations were washed by upward displacement at 15 minute intervals and, if necessary, the resting tension was readjusted to 2 g using a mechanical micromanipulator system.

Once a steady resting tension had been obtained, the preparations were dosed simultaneously with the test compound ($10^{-8} - 2 \times 10^{-5}$M), and finally a maximum relaxation achieved by addition of $10^{-3}$M isoprenaline. The fall in tension evoked by the test compound was expressed as a percentage of the total relaxation evoked in the presence of $10^{-3}$ isoprenaline. Appropriate concentration-relaxation curves were then constructed and values for potency ($IC_{50}$) were obtained.

[The composition of Krebs solution is: sodium chloride 118.07 mM, sodium hydrogen carbonate 26.19 mM, potassium chloride 4.68 mM, potassium orthophosphate 1.18 mM, magnesium sulphate septahydrate 1.8 mM and calcium chloride 2.52 mM;pH ca. 7.45.]

The compound of Example 1 gave an $IC_{50}$ value of $2.1 \times 10^{-7}$M.

We claim:

1. A compound of formula (I) or a pharmaceutically acceptable salt thereof:

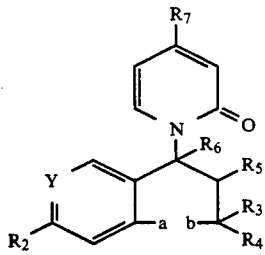

wherein
a and b together form an —O— linkage;
Y is C-$R_1$
wherein
either one of $R_1$ and $R_2$ is hydrogen and the other is nitro, cyano, halo, $CF_3$, $C_2F_5$, formyl, aldoxime, $CF_3$, $NO_2$—CH=CH—, NC—CH=CH—; a group $R_xX$— wherein $R_x$ is $C_{1-6}$ alkyl, which may be optionally substituted by one, two or three of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, $O.SO_2$, CONH, O.CONH C=S, O.C=S, C=S.O, CH.SH, SONH, $SO_2NH$, O.SONH, $O.SO_2NH$, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or a group $(R_wO)_2P(O)W$ wherein $R_w$ is hydrogen or $C_{1-6}$ alkyl and W is O or a bond; or $R_1$ is a $C_{3-8}$ cycloalkyl group or a $C_{1-6}$ alkyl group unsubstituted or substituted by a group which is selected from the group consisting of hydroxy, $C_{1-6}$ alkoxy, amino unsubstituted or substituted by one or two $C_{1-6}$ alkyl groups, $C_{1-7}$ alkanoylamino, $C_{3-8}$ cycloalkyloxy and $C_{3-8}$ cycloalkylamino; and $R_2$ is hydrogen; or either one of $R_1$ and $R_2$ is nitro, cyano or $C_{1-3}$ alkylcarbonyl and the other is a different group selected from the group consisting of nitro, cyano, halo, $C_{1-3}$ alkylcarbonyl, methoxy or amino unsubstituted or substituted by one or two $C_{1-6}$ alkyl or by $C_{2-7}$ alkanoyl;

either one of $R_1$ and $R_2$ is hydrogen or $C_{14}$ alkyl and the other is $C_{1-4}$ alkyl; or $R_3$ and $R_4$ together are $C_{2-5}$ polymethylene; either $R_5$ is hydrogen, hydroxy, $C_{1-6}$ alkoxy or $C_{1-7}$ acyloxy or $ONO_2$; and $R_6$ is hydrogen; or $R_5$ and $R_6$ together are a bond;

$R_7$ is unsubstituted or substituted phenyl in which the substituents are selected form the group consisting of $C_{1-6}$alkyl, $C_{1-6}$alkoxy, nitro, halo, amino unsubstituted or substituted by one or two $C_{1-4}$ alkyl groups, $C_{1-6}$ alkylcarbonylamino, $C_{1-6}$alkylcarbonyloxy, hydroyx, and $C_{1-6}$ alkylcarbonyl; and the pyridonyl moiety is trans to the $R_5$ group when $R_5$ is hydroxy, $C_{1-6}$ alkoxy, $C_{1-7}$ acyloxy or $ONO_2$.

2. A compound according to claim 1 wherein $R_1$ is nitro, cyano, acetyl, $CF_3$, $C_2F_5$ or $C_{1-4}$ alkyl, and $R_2$ is hydrogen.

3. A compound according to claim 2 wherein $R_1$ is cyano.

4. A compound according to claim 1 wherein $R_3$ and $R_4$ are both methyl groups.

5. A compound according to claim 1 wherein $R_5$ is hydroxy and $R_6$ is hydrogen, or $R_5$ and $R_6$ together are a bond.

6. A compound according to claim 1 wherein $R_7$ is unsubstituted phenyl.

7. A compound according to claim 1 wherein $R_7$ is phenyl substituted by a nitro or amino group.

8. A compound selected from the group consisting of:
6-cyano-2,2-dimethyl-4-(2-OxO-4-phenyl-1,2-dihydropyridyl)-2H-1-benzopyran,
(±)-trans-6-cyano-3,4-dihydro-2,2-dimethyl4-(4-(3-nitrophenyl)-2-oxo-1,2-dihydropyridyl)-2H-1-benzopyran-3-ol,
(±)-trans-4-(4-(3-aminophenyl)-2-oxo-1,2-dihydropyridyl)-6-cyano-3,4-dihydro-2,2-dimethyl-2H-1-benzopyran-3-ol,
(±)-trans-6-cyano-3,4-dihydro-2,2-dimethyl-4-(4-(4-nitrophenyl)-2-oxo-1,2-dihydropyridyl)-2H-1-benzopyran-3-ol,
6-cyano-2,2-dimethyl-4-(4-(4-nitrophenyl)-2-oxo-1,2-dihydropyridyl)-2H-1-benzopyran and
4-(4-(4-aminophenyl)-2-oxo-1,2-dihydropyridyl)-6-cyano-2,2-dimethyl-2H-1-benzopyran.

9. A pharmaceutical composition having bronchodilator activity or utility as a potassium channel activator, comprising an effective amount of a compound according to claim 1, and a pharmaceutically acceptable carrier.

10. A method of treatment of respiratory tract disorders in mammals which comprises 5 the administration to the mammal in need of such treatment, an effective amount of a compound according to claim 1.

* * * * *